United States Patent
Berthiaume et al.

(10) Patent No.: US 6,200,305 B1
(45) Date of Patent: Mar. 13, 2001

(54) CATHETER HAVING A VARIABLE LENGTH SHAFT SEGMENT AND METHOD OF USE

(75) Inventors: William A. Berthiaume, Hudson, MA (US); John Hudson, Wells Beach, ME (US)

(73) Assignee: Medtronic AVE, Inc., Santa Rosa, CA (US)

(*) Notice: Subject to any disclaimer, the term of this patent is extended or adjusted under 35 U.S.C. 154(b) by 0 days.

(21) Appl. No.: 09/164,007

(22) Filed: Sep. 30, 1998

(51) Int. Cl.[7] .................................................. A61M 31/00
(52) U.S. Cl. ................. 604/509; 604/99.04; 604/103.04; 604/528
(58) Field of Search ................................ 604/93, 96, 164, 604/264, 507–510, 523, 528, 96.01, 103.04, 103.09, 93.01

(56) References Cited

U.S. PATENT DOCUMENTS

| | | |
|---|---|---|
| 3,592,192 | 7/1971 | Harautuneian . |
| 3,593,713 * | 7/1971 | Bogoff et al. ................... 604/102.02 |
| 3,610,240 | 10/1971 | Harautuneian . |
| 3,896,815 | 7/1975 | Fettel et al. . |
| 4,449,972 * | 5/1984 | Kruger ........................... 604/103.11 |
| 4,564,014 | 1/1986 | Fogarty et al. . |
| 4,715,378 | 12/1987 | Pope, Jr. et al. . |
| 4,732,152 | 3/1988 | Wallstén et al. . |
| 4,848,343 | 7/1989 | Wallstén et al. . |
| 4,875,480 | 10/1989 | Imbert . |
| 5,002,559 | 3/1991 | Tower . |
| 5,112,304 | 5/1992 | Barlow et al. . |
| 5,152,277 | 10/1992 | Honda et al. . |
| 5,171,297 | 12/1992 | Barlow et al. . |
| 5,269,759 * | 12/1993 | Hernandez et al. .............. 604/96.01 |
| 5,334,153 | 8/1994 | McIntyre et al. . |
| 5,352,198 * | 10/1994 | Goldenberg et al. ............. 604/95.04 |
| 5,372,592 | 12/1994 | Gambale . |
| 5,387,226 | 2/1995 | Miraki . |
| 5,389,087 | 2/1995 | Miraki . |
| 5,395,332 | 3/1995 | Ressemann et al. . |
| 5,407,432 | 4/1995 | Solar . |
| 5,409,459 | 4/1995 | Gambale . |
| 5,413,560 | 5/1995 | Solar . |
| 5,425,711 | 6/1995 | Ressemann et al. . |
| 5,443,456 | 8/1995 | Alliger et al. . |
| 5,447,503 | 9/1995 | Miller . |
| 5,451,233 | 9/1995 | Yock . |
| 5,462,530 | 10/1995 | Jang . |
| 5,466,222 | 11/1995 | Ressemann et al. ............ 604/103.09 |
| 5,484,409 | 1/1996 | Atkinson et al. . |
| 5,489,271 | 2/1996 | Anderson . |

(List continued on next page.)

Primary Examiner—A. T. Nguyen
Assistant Examiner—Jeremy Thissell
(74) Attorney, Agent, or Firm—Sterne, Kessler, Goldstein & Fox P.L.L.C.

(57) ABSTRACT

The invention relates to a catheter device and guidewire system to enable the catheter to be exchanged over a conventional length guidewire without the use of a guidewire extension or exchange wire. The catheter device includes an elongated inflation shaft having a longitudinal inflation lumen, an extension shaft having a longitudinal extension lumen coupled in fluid communication with the inflation lumen, a balloon member disposed at the distal end of the extension shaft and in fluid communication with the inflation lumen, a guidewire shaft having a longitudinal guidewire lumen which extends from the distal end of the balloon member, through the balloon member and extension shaft, to the proximal end of the extension shaft, and a variable length shaft coupled to the proximal end of the extension shaft. The variable length shaft comprises an elastomeric material which may be rolled about its outside surface such that the shaft may selectively extend from a rolled up state having a length of about 1 centimeters to a fully unrolled state having a length of about 140 centimeters.

8 Claims, 2 Drawing Sheets

U.S. PATENT DOCUMENTS

| | | |
|---|---|---|
| 5,492,532 | 2/1996 | Ryan et al. . |
| 5,501,227 | 3/1996 | Yock . |
| 5,507,731 | 4/1996 | Hernandez et al. . |
| 5,514,093 | 5/1996 | Ellis et al. . |
| 5,549,551 | 8/1996 | Peacock, III et al. . |
| 5,558,635 | 9/1996 | Cannon . |
| 5,571,087 | 11/1996 | Ressemann et al. . |
| 5,579,779 | 12/1996 | Humphrey . |
| 5,591,194 | 1/1997 | Berthiaume . |
| 5,598,844 | 2/1997 | Diaz et al. . |
| 5,607,406 | 3/1997 | Hernandez et al. . |
| 5,645,533 | 7/1997 | Blaeser et al. . |
| 5,658,251 | 8/1997 | Ressemann et al. . |
| 5,658,309 | 8/1997 | Berthiaume et al. . |
| 5,676,654 | 10/1997 | Ellis et al. . |
| 5,693,021 | 12/1997 | Diaz et al. . |
| 5,779,671 | 7/1998 | Ressemann et al. . |

* cited by examiner

CATHETER HAVING A VARIABLE LENGTH SHAFT SEGMENT AND METHOD OF USE

FIELD OF THE INVENTION

The present invention relates to catheter systems employed in intravascular procedures. More particularly, the present invention relates to a catheter device and exchange system for facilitating the exchange of catheters and/or guidewires, and for the transport of such catheters and/or guidewires to a selected site within the patient's vasculature without the need for guidewire extensions or exchange wires.

BACKGROUND OF THE INVENTION

Catheters are widely used by the medical profession for a variety of purposes and procedures. For example, catheters are commonly used in the treatment of atherosclerotic lesions or stenoses formed on the interior walls of the arteries. One procedure developed for the treatment of such lesions or stenoses is coronary angioplasty. The most commonly practiced angioplasty procedure is known as percutaneous transluminal coronary angioplasty, or PTCA. According to this procedure, a dilatation catheter having a balloon located at its distal end is guided through the patient's vasculature such that the balloon is positioned within the stenosis. When the catheter is advanced through the patient's vasculature to the treatment site, the balloon is in a deflated state such that the catheter has a minimum cross-section. Once the balloon is positioned across the treatment site, the balloon is inflated one or more times to dilate the stenosis and open the restricted area of the artery. Finally, the balloon is deflated and the catheter is removed from the patient's vasculature.

Typically, the dilatation catheter is maneuvered through the patient's vasculature with the use of a flexible guidewire having a diameter of approximately 0.010 to 0.018 inches and a length of about 180 centimeters. The distal end of the guidewire is extremely flexible so that it may be routed through the convoluted arterial pathway to the site of the stenosis. After the distal portion of the guidewire is positioned across the stenosis, a dilatation catheter having a lumen adapted to receive the guidewire is advanced over the guidewire until the balloon is positioned within the stenosis. Alternatively, the guidewire and catheter may be advanced together within the patient's vasculature to the treatment site with the distal end of the guidewire protruding from the distal end of the catheter.

The prior art includes three types of catheters for use with a guidewire: "over-the-wire" catheters, "rapid exchange" catheters and "fixed-wire" catheters.

A conventional over-the-wire catheter comprises a guidewire lumen, which extends throughout the length of the catheter. In use, the guidewire is disposed entirely within the catheter guidewire lumen except for its proximal and distal ends which protrude from the proximal and distal ends of the catheter, respectively. A typical over-the-wire balloon dilatation catheter is disclosed in Simpson et al. U.S. Pat. No. 4,323,071.

Such over-the-wire catheters have many advantages attributable to the full-length guidewire lumen. For example, these type catheters have good stiffness and pushability for advancing the catheter through the convoluted vasculature to the treatment site. Further, the guidewire lumen provides a continuous conduit between the proximal and distal ends of the catheter for transporting radiocontrast dye to the treatment site or for enabling pressure measurements. In addition, the full-length guidewire lumen allows for the exchange of guidewires within an indwelling catheter, should that be desired.

Despite these advantages, there are many undesirable complications associated with the use of over-the-wire catheters. For example, during a catheterization procedure, it may be necessary to thread a catheter on or off an indwelling catheter, or exchange an indwelling catheter for another catheter over an indwelling guidewire. When advancing or withdrawing a catheter over an indwelling guidewire, the physician must grip the proximal portion of the guidewire extending outside the patient to maintain the position of the distal portion of the guidewire across the treatment site. However, the length of a conventional over-the-wire catheter, typically on the order of 135 centimeters, is greater than the length of the proximal portion of a standard guidewire which protrudes out of the patient. Accordingly, it is necessary to extend the guidewire a sufficient distance outside the patient so that the physician may maintain his or her grip on the proximal portion of the guidewire while threading an over-the-wire catheter on or off an indwelling guidewire. The additional length of guidewire needed is typically provided through the use of a guidewire extension which is temporarily "linked" or attached to the proximal end of the guidewire. Once the catheter has been threaded onto the guidewire extension and advanced over the guidewire through the patient's vasculature, the guidewire extension may be detached from the guidewire.

Alternatively, an exchange wire on the order of 300 centimeters may first be guided through the patient's vasculature such that its distal portion is positioned across the stenosis. The catheter may then be advanced over the exchange wire without disturbing the position of the distal end of the wire. After the balloon located at the distal end of the catheter is positioned within the stenosis, the exchange wire may be removed from the guidewire lumen and replaced with a shorter, easier to handle guidewire.

A number of alternative catheter designs have been developed in an attempt to address these issues. One such design is the fixed-wire catheter, which comprises a catheter having an internally fixed guidewire or stiffening element. Catheters of this design are readily maneuverable and relatively easy to position within the patient's vasculature without the use of a separate guidewire. However, because these catheters do not use a separate guidewire, the administering physician is unable to maintain guidewire access to the treatment site while removing the catheter. Thus, if it were necessary to exchange the catheter, the physician must remove the indwelling catheter and renegotiate the arterial pathway to the treatment site with the replacement catheter.

Another alternate design is the "rapid exchange" type catheter and guidewire system. Generally, a rapid exchange catheter includes a guidewire lumen which extends along only a short shaft section near the distal end of the catheter. Accordingly, when the catheter is advanced over the guidewire, the guidewire is located outside the catheter except for the short segment which passes through the guidewire lumen at the distal end of the catheter. In use, a conventional length guidewire is routed through the patient's vasculature such that its distal end is positioned across the treatment site. The distal end of the catheter is then threaded onto the proximal end of the guidewire. Since the guidewire lumen is relatively short, the catheter may be fully threaded onto the guidewire without linking an extension wire or using a long exchange wire. Similarly, when it is desired to perform a catheter exchange procedure, the catheter may be withdrawn over an indwelling guidewire without the use of a guidewire extension or an exchange wire.

Although such a rapid exchange catheter system may eliminate the need for an extension wire or a long exchange wire, it presents significant disadvantages. For example, because these catheters have a truncated guidewire lumen, they do not provide the same stiffness and pushability as an over-the-wire catheter. Further, it has been found that as these catheters are advanced or withdrawn along the guidewire, the exposed portion of the guidewire may buckle or bow relative to the catheter and possibly inflict damage to the inner walls of the patient's vasculature. Furthermore, there exists a significant risk of guidewire entanglement in procedures involving multiple guidewires. In addition, unlike over-the-wire catheters, it is not possible to exchange guidewires in an indwelling rapid exchange catheter.

Therefore, there exists a need for an improved catheter device and method of use which incorporates the benefits of both the over-the-wire catheters and the rapid exchange catheters, but without their attendant drawbacks.

OBJECTS AND SUMMARY OF THE INVENTION

In accordance with the present invention, a catheter device having a variable length guidewire lumen is provided for enabling rapid exchange of the catheter over a conventional length guidewire. The catheter includes an elongated inflation shaft having a longitudinal inflation lumen, an extension shaft disposed distal to the inflation shaft, a balloon member disposed at the distal end of the extension shaft, a guidewire shaft having a longitudinal guidewire lumen which extends from the distal end of the balloon member, through the balloon member and the extension shaft, to the proximal end of the extension shaft, and a variable length shaft coupled adjacent the proximal end of the extension shaft. The extension shaft includes an extension lumen having a proximal end in fluid communication with the distal end of the inflation lumen and a distal end in fluid communication with the interior of the balloon. The variable length shaft comprises a rollable tube formed of an elastomeric material and having a length selectively variable from about 1 centimeter to about 140 centimeters.

When the catheter is threaded over an indwelling guidewire or when the catheter is being exchanged with another catheter, the variable length shaft is in a rolled up state having a length of about 1 centimeter. The distance from the proximal end of the variable length shaft to the distal end of the guidewire shaft is sufficiently short that the catheter may be threaded onto or removed from the indwelling guidewire without the use of an extension wire. Further, as the catheter is advanced over the guidewire through the patient's vasculature, the variable length shaft is unrolled from its shortest length of about 1 centimeter to its longest length of about 140 centimeters, thereby capturing the entire length of the guidewire extending between the proximal end of the catheter and the proximal end of the guidewire lumen.

It is, therefore, a principal object of the present invention to provide an improved catheter and guidewire system which enables loading and unloading of the catheter over an indwelling guidewire without the use of an extension wire, and the exchange of the guidewire without compromising the position of the indwelling catheter.

It is a further object of the present invention to provide an improved catheter and guidewire system, wherein the catheter includes a variable length shaft which provides a smooth interior surface when it is at any position between a fully extended or fully retracted state.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

BRIEF DESCRIPTION OF THE DRAWINGS

The invention will be further described, by way of example, with reference to the accompanying drawings, wherein.

DESCRIPTION OF THE PREFERRED EMBODIMENTS

It should be noted that while the following description will be specifically in the context of coronary angioplasty dilatation catheters, the invention is not so limited and is applicable to other catheter assemblies and procedures. For example, it will be understood that the present invention also applies to drug delivery and/or stent delivery catheters.

Referring generally to the embodiments of the invention shown in the accompanying drawings, wherein like reference numbers refer to like parts throughout the various views, the basic principles of the broadest aspects of the invention can be appreciated from FIGS. 1–5.

Figure 1:
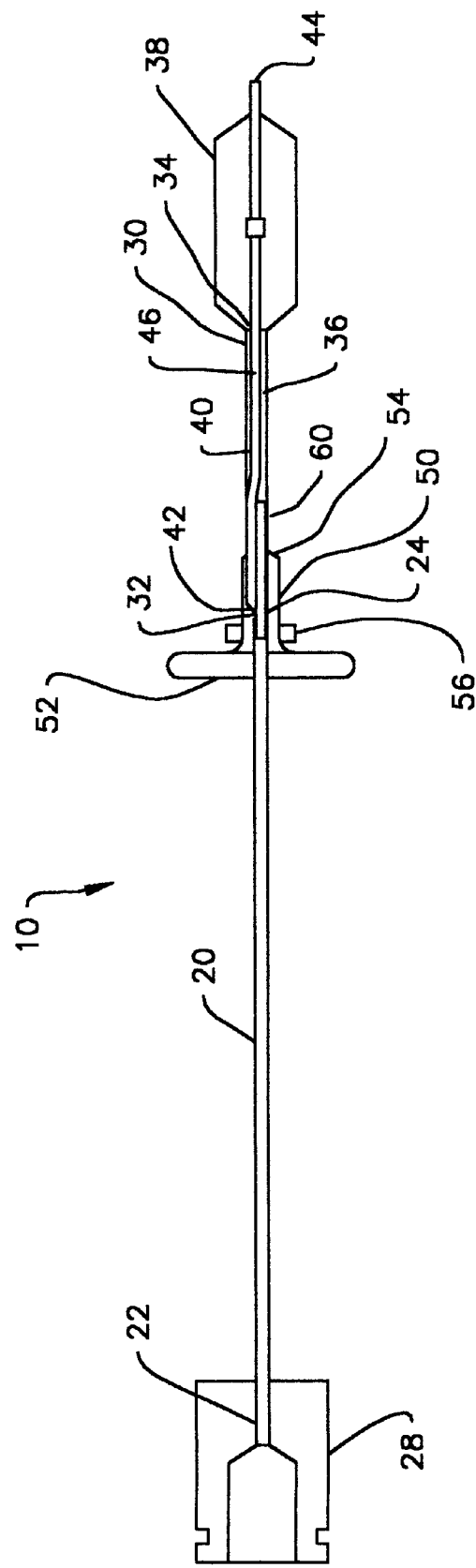
FIG. 1 is a cross-sectional view of the variable length shaft catheter of the present invention with the variable length shaft in its rolled up state.

As shown in FIG. 1, the variable length shaft catheter of the present invention, which is designated generally as 10, includes an elongated inflation shaft 20, an extension shaft 30, a balloon member 38, a guidewire shaft 40, and a variable length shaft 50.

The inflation shaft 20 includes a proximal end 22, a distal end 24, and an inflation lumen 26 extending longitudinally throughout its length. Preferably, inflation shaft 20 is formed from stainless steel hypotube to provide the catheter with sufficient stiffness and pushability. The proximal end 22 of inflation shaft 20 is coupled to a fitting 28, which is designed to enable fluid communication between inflation lumen 26 and a source of pressurized inflation fluid (not shown). Preferably, fitting 28 is in the form of a female luer fitting.

Figure 2:
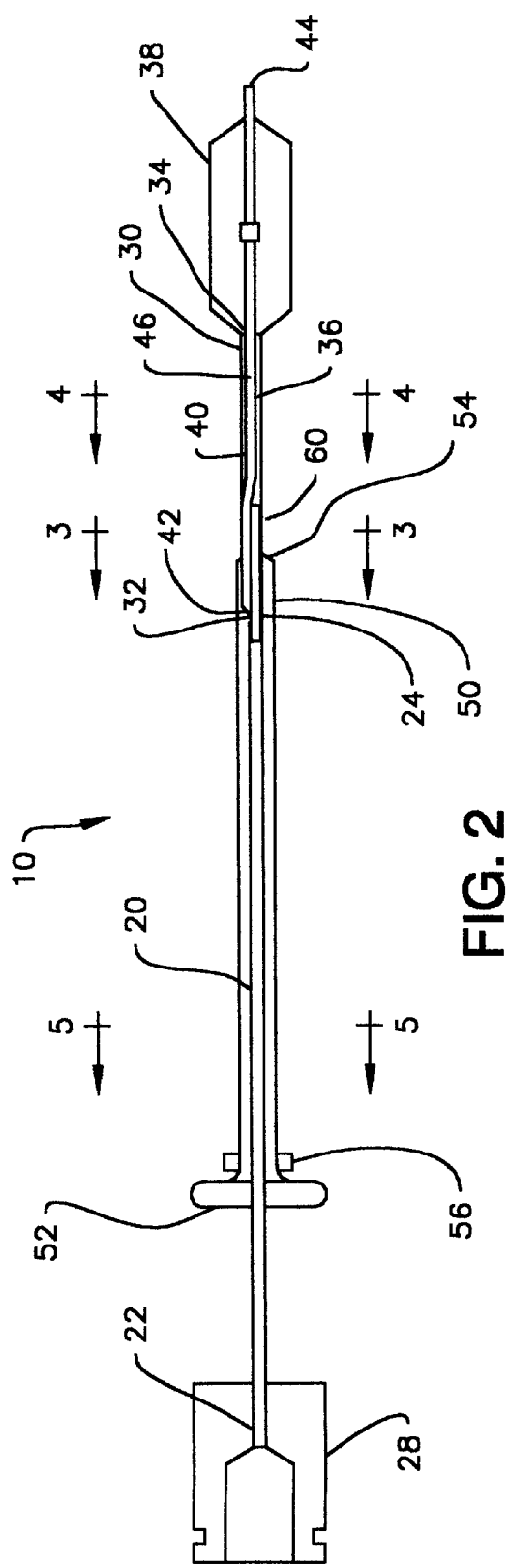
FIG. 2 is a cross-sectional view of the variable length shaft catheter tube of the present invention with the variable length shaft in an elongated state.

The extension shaft 30 includes a proximal end 32, a distal end 34, and an extension lumen 36 extending longitudinally throughout its length. As illustrated in FIGS. 1 and 2, the proximal end 32 of extension shaft 30 is disposed adjacent the distal end 24 of inflation shaft 20. Further, extension lumen 36 is coupled in fluid communication with inflation lumen 26, such that inflation lumen 26 and extension lumen 36 form a continuous conduit enabling fluid communication from the proximal end of inflation shaft 20 to the distal end of extension shaft 30. Extension shaft 30 may be formed from a flexible polymer material such as polyvinyl chloride, polyethylene terephthalate or, preferably, high density polyethylene.

In a preferred embodiment, the distal end of inflation shaft 20 and the proximal end of extension shaft 30 are coupled via an extension tube 60. According to this configuration, extension tube 60 provides a fluid communication pathway between inflation lumen 26 and extension lumen 36. Extension tube 60 is preferably formed from stainless steel hypotube.

The balloon member 38 is disposed at the distal end of extension shaft 30. Balloon member 38 may be formed from polyvinyl chloride, polyethylene, polyurethane or preferably, polyethylene terephthalate. The interior of balloon member 38 is in fluid communication with inflation lumen 26 by way of extension lumen 36. To this end, balloon member 38 may be inflated by injecting inflation fluid through fitting 28, inflation lumen 26 and extension lumen 36, and into balloon member 38. Subsequently, balloon member 38 may be deflated by purging the inflation fluid from balloon member 38 through extension lumen 36, inflation lumen 26 and fitting 28.

The guidewire shaft 40 has a proximal end 42, a distal end 44, and a guidewire lumen 46 extending longitudinally throughout its length. Guidewire shaft 40 may be formed from a flexible polymer material, such as polyvinyl chloride, polyethylene terephthalate or, preferably, high density polyethylene. As illustrated in FIGS. 1 and 2, guidewire shaft 40 is longitudinally disposed within extension shaft 30 and extends through balloon member 38, whereby the distal end 44 of guidewire shaft 40 extends beyond the distal end of balloon member 38. The distal end of balloon member 38 is coupled to guidewire shaft 40.

Figure 4:
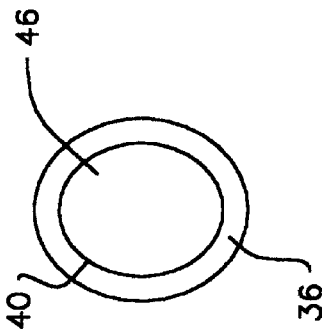
FIG. 4 is a cross-sectional view of the variable length shaft catheter shown in FIG. 2 along line 4—4.
Figure 3:
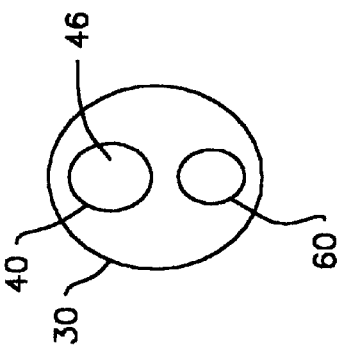
FIG. 3 is a cross-sectional view of the variable length shaft catheter shown in FIG. 2 along line 3—3.
Figure 5:
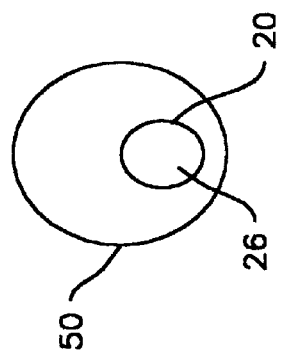
FIG. 5 is a cross-sectional view of the variable length shaft catheter shown in FIG. 2 along line 5—5.

Guidewire lumen 46 is dimensioned to slidably receive a standard coronary angioplasty guidewire (not shown). As shown in FIG. 3, at the proximal portion of extension shaft 30, guidewire shaft 40 and extension tube 60 are disposed in a parallel arrangement, thereby providing a side-by-side dual lumen cross section. As shown in FIG. 4, at the distal end of extension shaft 30, guidewire shaft 40 extends longitudinally through extension lumen 36, thereby providing a coaxial dual lumen cross section. To this end, the outer diameter of guidewire shaft 40 is dimensioned such that extension lumen 36 forms an annular flow passage with sufficient inflation flow capacity to permit acceptable balloon inflation and deflation rates. Alternatively, it will be understood that guidewire shaft 40 may be disposed in parallel arrangement with extension tube 60 and extension lumen 36 to provide a side-by-side dual lumen cross-section throughout the length of extension shaft 30.

The variable length shaft 50 is preferably formed of an elastomeric material having a proximal end 52 and a distal end 54. Variable length shaft 50 may be selectively varied in length by rolling or unrolling the distal end 54 about the outside surface of the shaft from a fully rolled state having a length of about 1 centimeter to a fully unrolled state having a length of about 140 centimeters. As shown in FIGS. 1 and 2, the distal end of variable length shaft 50 is coupled to the proximal end of extension shaft 30. In a preferred embodiment, variable length shaft 50 is coupled about the outside surface of extension shaft 30 such that as it is unrolled it encompasses inflation shaft 20 (see FIG. 5). Alternatively, variable length shaft 50 may be coupled to the proximal end of extension shaft 30 such that as it is unrolled it extends longitudinally in a side-by-side arrangement with inflation shaft 20. Further, the catheter of the present invention may be adapted to have a plurality of variable extension shafts, each of which is designed to receive a separate guidewire for procedures requiring multiple guidewires.

If desired, the catheter device of the present invention may include an anti-backbleed hub 56 which functions to prevent the backflow of fluid between a guiding catheter and catheter 10, and through a Tuohy-Borst adapter. To this end, as shown in FIG. 2, anti-backbleed hub 56 comprises a tubular member slidably coupled about the outside surface of variable length shaft 50. According to this arrangement, tubular member 56 may be maintained at a position immediately adjacent the variable length shaft proximal end 52 as the variable length shaft 50 is rolled or unrolled. Preferably, anti-backbleed hub 56 includes a flanged annular lip at its proximal end for abutment with the Tuohy-Borst adapter.

In addition, anti-backbleed hub 56 may be designed to act as a stop or anchor which prevents the longitudinal movement of inflation shaft 20 within variable length shaft 50. To this end, anti-backbleed hub 56 is formed of a compressible material, such that when the Tuohy-Borst adapter is closed and locked down on the outside surface of anti-backbleed hub 56, anti-backbleed hub 56 is radially compressed such that its inside surface grips and locks down on inflation shaft 50.

Operation and use of the variable length shaft catheter of the present invention is described as follows. A guiding catheter (not shown in the FIGS.) is inserted into the patient's vasculature in a conventional manner. A Tuohy-Borst adapter (not shown in the FIGS.) is then disposed at the proximal end of the guiding catheter. Next, the Tuohy-Borst adapter is opened to receive a standard length guidewire. The guidewire is routed through the patient's vasculature until the guidewire distal portion is positioned across the treatment site. The Tuohy-Borst adapter is then closed such that it locks down on the guidewire.

Prior to loading catheter 10 onto the indwelling guidewire, variable length shaft 50 is in a fully rolled state so that the effective "over-the-wire length" of catheter 10 is at a minimum. The catheter 10 is loaded onto the guidewire by inserting the proximal end of the guidewire into the distal end of the guidewire lumen 46. The catheter 10 is then advanced over the guidewire until the distal end of the catheter is immediately proximal the Tuohy-Borst adapter. Because catheter 10 is in a fully rolled state and has a minimum over-the-wire length, the proximal end of the guidewire protrudes out the proximal end of guidewire lumen 46. The physician opens the Tuohy-Borst adapter and, while holding the proximal end of the guidewire, pushes the catheter through the Tuohy-Borst adapter until the anti-backbleed hub 56 is adjacent the Tuohy-Borst adapter. The Tuohy-Borst adapter is then closed until it locks down on and is securely coupled to the anti-backbleed hub 56.

Catheter 10 is then advanced over the indwelling guidewire by holding the proximal end of the guidewire and pushing the proximal end of inflation shaft 20 toward the Tuohy-Borst adapter until the balloon member 38 is positioned across the treatment site. It will be understood that as catheter 10 is advanced through the patient's vasculature, variable length shaft 50 unrolls and encases the portions of the guidewire and inflation shaft 20 extending from the proximal end of extension shaft 30 to the Tuohy-Borst adapter.

Accordingly, as catheter 10 is advanced over the guidewire, variable length shaft 50 and guidewire lumen 46 effectively form a full-length guidewire lumen. As such, medications, saline or radiocontrast dye can be delivered to the treatment site by way of injection through the passageway created by variable length shaft 50 and guidewire lumen 46.

Variable length shaft 50 may be unrolled as catheter 10 is advanced through the patient's vasculature by any of a number of means. For example, the elastomeric material of the variable length shaft 50 may have a memory processed into it or may be made of a shape memory polymer alloy, which permits it to unroll and roll up on its own. Alternatively, the variable length shaft 50 may be manually unrolled as the administering physician advances the catheter through the patient's vasculature. Furthermore, a mechanical device may be used by the administering physician to unroll or roll variable length shaft 50.

Once balloon member 38 has been positioned across the treatment site, pressurized inflation fluid may be injected through fitting 28 by the use of any pressurizing device known in the art (not shown in the FIGS.). The inflation fluid passes through fitting 28, inflation lumen 26, extension tube 60 and extension lumen 36, before entering balloon member 38. The inflation of balloon member 38 can be observed if radiographic contrast liquid is used as the inflation fluid. As balloon member 38 is inflated with pressurized inflation fluid, it presses against the treatment site and dilates the stenosis.

During a catheterization procedure, it may be necessary to exchange the indwelling catheter with another catheter having a different feature. For example, it may be desired to follow a balloon dilatation procedure with a drug delivery or stent delivery procedure. Likewise, in the event the balloon on the indwelling catheter is too small to sufficiently dilate the stenosis, the administering physician may elect to exchange the indwelling catheter with another catheter having a larger balloon. As provided in the present invention, variable length shaft 50 of catheter 10 provides a means for catheter exchange without the use of a guidewire extension or exchange wire.

It is understood that during catheter exchange procedures, it is desirable to maintain the position of the distal end of the guidewire across the treatment site. To effect an exchange of catheter 10, the administering physician holds the proximal end of the guidewire in a fixed position. In addition, the physician grips and pulls the proximal end of inflation shaft 20 such that the catheter is withdrawn from the patient over the guidewire. As the catheter is withdrawn from the patient, proximal end 52 of variable length shaft 50 rolls about the outside surface of variable length shaft 50, whereby variable length shaft 50 is reduced in length until it reaches its rolled up length of about 1 centimeter. The Tuohy-Borst adapter is then opened and decoupled from the antiback-bleed hub 56. While maintaining the position of the distal end of the guidewire across the treatment site, the administering physician removes the catheter 10 from the proximal end of the guidewire. It will be understood that the effective over-the-wire length of the catheter when variable length shaft 50 is in its rolled up state is sufficiently short to enable removal of the catheter without the use of an extension wire. After the original catheter is removed, a second catheter in the form of the present invention may be threaded over the guidewire as described above.

While only a few embodiments have been illustrated and described in connection with the present invention, various modifications and changes in both the apparatus and method will become apparent to those skilled in the art. All such modifications or changes falling within the scope of the claims are intended to be included therein.

We claim:

1. A catheter device having a variable length guidewire lumen adapted for use with a conventional length guidewire, comprising:

(a) an elongated inflation shaft having a proximal end, a distal end and an inflation lumen extending longitudinally throughout its length;

(b) an extension shaft having a proximal end, a distal end and an extension lumen extending longitudinally throughout its length, the extension shaft proximal end being disposed adjacent the distal end of the inflation shaft such that the inflation lumen and the extension lumen are in fluid communication and form a continuous passageway therethrough;

(c) a guidewire shaft having a proximal end, a distal end and a guidewire lumen extending throughout its length, the guidewire shaft disposed longitudinally throughout the length of the extension shaft, the distal end of the guidewire shaft extending beyond the distal end of the extension shaft, and the guidewire lumen dimensioned to slidably receive the guidewire;

(d) a balloon member having a distal end and a proximal end, the proximal end of the balloon member being coupled to the distal end of the extension shaft, the distal end of the balloon member being coupled to the guidewire shaft adjacent the distal end of the guidewire shaft, the balloon member defining an interior cavity in fluid communication with the extension lumen; and (e) a variable length shaft formed of an elastomeric material and having a proximal end, a distal end, an outside surface and a variable length guidewire lumen, wherein the distal end of the variable length shaft is coupled to the extension shaft and the proximal end of the variable length shaft may be rolled and unrolled about the outside surface thereof to selectively vary the length of the variable length guidewire lumen.

2. The catheter device of claim 1, wherein the variable length shaft may be selectively varied in length from a rolled up state of about 1 centimeter to a fully unrolled state of about 140 centimeters.

3. The catheter device of claim 1, which further comprises an anti-backbleed hub coupled to the proximal end of the variable length shaft, the anti-backbleed hub having a central port dimensioned to permit the inflation shaft and guidewire to pass therethrough.

4. The catheter device of claim 1, which further comprises an extension tube which provides a fluid communication pathway between the inflation lumen in fluid communication with the extension lumen.

5. The catheter device of claim 1, wherein the distal end of the variable length shaft is coupled about the outside surface of the extension shaft, the variable length shaft extends longitudinally in coaxial relation with the inflation shaft such that as the variable length shaft is unrolled from a rolled up state to an unrolled state it encases the inflation shaft.

6. The catheter device of claim 1, wherein the inflation shaft is formed from hypotube.

7. The catheter device of claim 6, which further comprises a fitting coupled to the proximal end of the inflation shaft to enable fluid communication between the inflation lumen and a source of pressurized fluid.

8. A method for loading and unloading a balloon catheter device having a variable length shaft segment over a conventional length guidewire without the use of an exchange wire or a guidewire extension, the method comprising the steps of:

(a) inserting a guiding catheter in a patient's vasculature;

(b) disposing an adapter at the proximal end of the guiding catheter, such that the adapter is positioned immediately outside the patient's body and concentric with an incision;

(c) opening the adapter and inserting the conventional length guidewire having a distal end and a proximal end into the guiding catheter and advancing the distal end of the guidewire to a treatment site within the patient's vasculature;

(d) loading the balloon catheter over the proximal end of the guidewire and advancing the balloon catheter through the adapter into the guiding catheter;

(e) coupling the balloon catheter to the adapter;

(f) maintaining the distal end of the guidewire in position across the treatment site by gripping the guidewire at a position immediately proximate the adapter;

(g) advancing the balloon catheter over the guidewire such that a balloon member of the balloon catheter is across the treatment site by pushing an inflation shaft of the balloon catheter toward the adapter and thereby unrolling the variable length shaft segment;

(h) unloading the balloon catheter by gripping the inflation shaft proximate the adapter and withdrawing the inflation shaft through the adapter until the variable length shaft segment is in the rolled up state;

(i) decoupling the balloon catheter and the adapter;

(j) gripping the proximal end of the guidewire with one hand and pulling the inflation shaft until the balloon catheter is withdrawn from the patient; and (k) gripping the guidewire at a position distal the balloon catheter and pulling the balloon catheter off the proximal end of the guidewire.

* * * * *